US012564654B2

(12) United States Patent
Usa et al.

(10) Patent No.: US 12,564,654 B2
(45) Date of Patent: Mar. 3, 2026

(54) DEODORIZATION APPARATUS

(71) Applicant: Sunstar Engineering Inc., Osaka (JP)

(72) Inventors: Tomoharu Usa, Osaka (JP); Katsuhiro Yamaguchi, Osaka (JP)

(73) Assignee: Sunstar Engineering Inc., Osaka (JP)

( * ) Notice: Subject to any disclaimer, the term of this patent is extended or adjusted under 35 U.S.C. 154(b) by 525 days.

(21) Appl. No.: 18/322,762

(22) Filed: May 24, 2023

(65) Prior Publication Data

US 2023/0381366 A1 Nov. 30, 2023

(30) Foreign Application Priority Data

May 25, 2022 (JP) ................................ 2022-085139

(51) Int. Cl.
*A61L 9/20* (2006.01)

(52) U.S. Cl.
CPC ........... *A61L 9/205* (2013.01); *A61L 2209/12* (2013.01)

(58) Field of Classification Search
CPC ...................................................... A61L 9/205
See application file for complete search history.

(56) References Cited

U.S. PATENT DOCUMENTS

| | | | | |
|---|---|---|---|---|
| 2018/0344890 | A1* | 12/2018 | Watanabe | ................ A61L 9/205 |
| 2019/0374670 | A1* | 12/2019 | Liu | .......................... A61L 9/205 |
| 2020/0355378 | A1 | 11/2020 | Jeong et al. | |
| 2021/0060199 | A1* | 3/2021 | Somei | ..................... A61L 9/205 |

FOREIGN PATENT DOCUMENTS

| | | | |
|---|---|---|---|
| JP | 2002-172153 A | 6/2002 | |
| JP | 2003070886 A | 3/2003 | |
| JP | 2021-511161 A | 5/2021 | |
| KR | 102358721 B1 * | 2/2022 | ............. A61L 9/205 |

OTHER PUBLICATIONS

Machine Translation of KR 102358721 (Year: 2022).*
Notification of Reasons for Refusal for corresponding Japanese Application No. 2022-085139 mailed May 7, 2024 and its English Machine Translation.

* cited by examiner

*Primary Examiner* — Timothy C Cleveland
(74) *Attorney, Agent, or Firm* — Renner, Otto, Boisselle & Sklar, LLP

(57) ABSTRACT

A deodorization apparatus according to one aspect of the present invention includes: a first main wall 201; a second main wall 202; a first side wall 203; a second side wall 204; a first partition wall 205 with a gap with the second main wall; a second partition wall 206 with a gap with the first main wall; a photocatalyst unit 30 provided between the first main wall and the second main wall, and allowing air to pass therethrough in a direction from the second main wall to the first main wall; and a centrifugal blower 40 disposed opposite to the photocatalyst unit with respect to the second partition wall and spaced apart from the first main wall, the centrifugal blower 40 having a suction port that opens toward the first main wall and a discharge port that opens on a side facing away from the second partition wall.

5 Claims, 6 Drawing Sheets

DEODORIZATION APPARATUS

This application claims benefit of priority to Japanese Patent Application No. 2022-085139, filed May 25, 2022, the entire contents of each are incorporated herein by reference.

BACKGROUND OF THE INVENTION

Field of the Invention

The present invention relates to a deodorization apparatus.

Related Art

A deodorization apparatus (air purifier) for decomposing odor components in air by a photocatalyst is used. In order to efficiently bring air into contact with a photocatalyst, a photocatalyst carrier is employed which includes a porous ceramic molding and a photocatalyst carried on the molding. A deodorization apparatus including such a photocatalyst carrier is configured to cause a fan to generate an airflow that passes through the photocatalyst carrier having a thick plate shape in the thickness direction (see, for example, Japanese Unexamined Patent Application, Publication No. 2003-70886).

SUMMARY OF THE INVENTION

In the deodorization apparatus as disclosed in Japanese Unexamined Patent Application, Publication No. 2003-70886, an increase in the area of the photocatalyst carrier increases the cross-sectional area of an airflow path, and as a result, the entire deodorization apparatus increases in size. For example, in a case where the deodorization apparatus is used on a wall, it is desirable to reduce the thickness of the deodorization apparatus. To address this, an object of the present invention is to provide a thin deodorization apparatus.

One aspect of the present invention is directed to a deodorization apparatus including: a first main wall; a second main wall facing the first main wall; a first side wall and a second side wall each sealing a space between a side edge of the first main wall and a side edge of the second main wall; a first partition wall disposed without a gap between the first partition wall and the first main wall and with a gap between the first partition wall and the second main wall; a second partition wall disposed without a gap between the second partition wall and the second main wall and with a gap between the second partition wall and the first main wall; a photocatalyst unit provided between the first main wall and the second main wall, and allowing air to pass therethrough in a direction from the second main wall to the first main wall; and a centrifugal blower disposed opposite to the photocatalyst unit with respect to the second partition wall and spaced apart from the first main wall, the centrifugal blower having a suction port that opens toward the first main wall and a discharge port that opens on a side facing away from the second partition wall.

The above-described deodorization apparatus may further include: a light source disposed adjacent to the second main wall and configured to emit light onto the photocatalyst unit; and a light shielding wall disposed opposite to the second partition wall with respect to the first partition wall, without a gap between the light shielding wall and the second main wall and with a gap between the light shielding wall and the first main wall.

The above-described deodorization apparatus may further include a circuit board disposed on an outer side of the second main wall and having the light source mounted thereon. The second main wall may have a light projection aperture through which the light source is exposed.

In the above-described deodorization, the first side wall may have, between the first partition wall and the second partition wall, an attachment/detachment opening through which the photocatalyst unit is inserted, and the first partition wall and the second partition wall may each have a guide for guiding the photocatalyst unit.

In the above-described deodorization, the photocatalyst unit may include a photocatalyst carrier and a frame that holds the photocatalyst carrier, and the photocatalyst carrier may include a plate-shaped porous ceramic molding and a photocatalyst carried on the plate-shaped porous ceramic molding.

The present invention provides a thin deodorization apparatus.

DETAILED DESCRIPTION OF THE INVENTION

Figure 1:
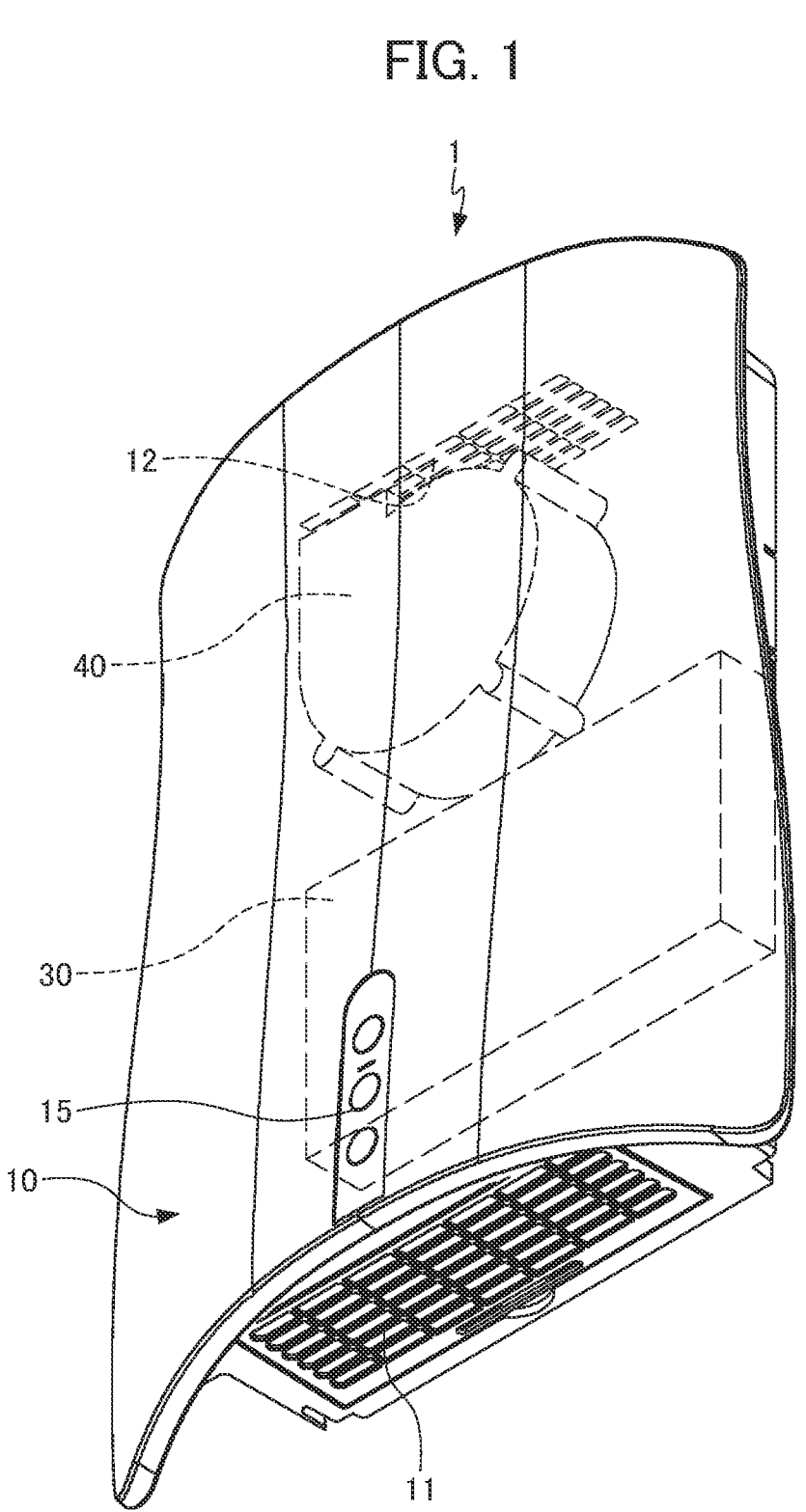
FIG. 1 is a perspective view illustrating a deodorization apparatus according to one embodiment of the present invention.
Figure 2:
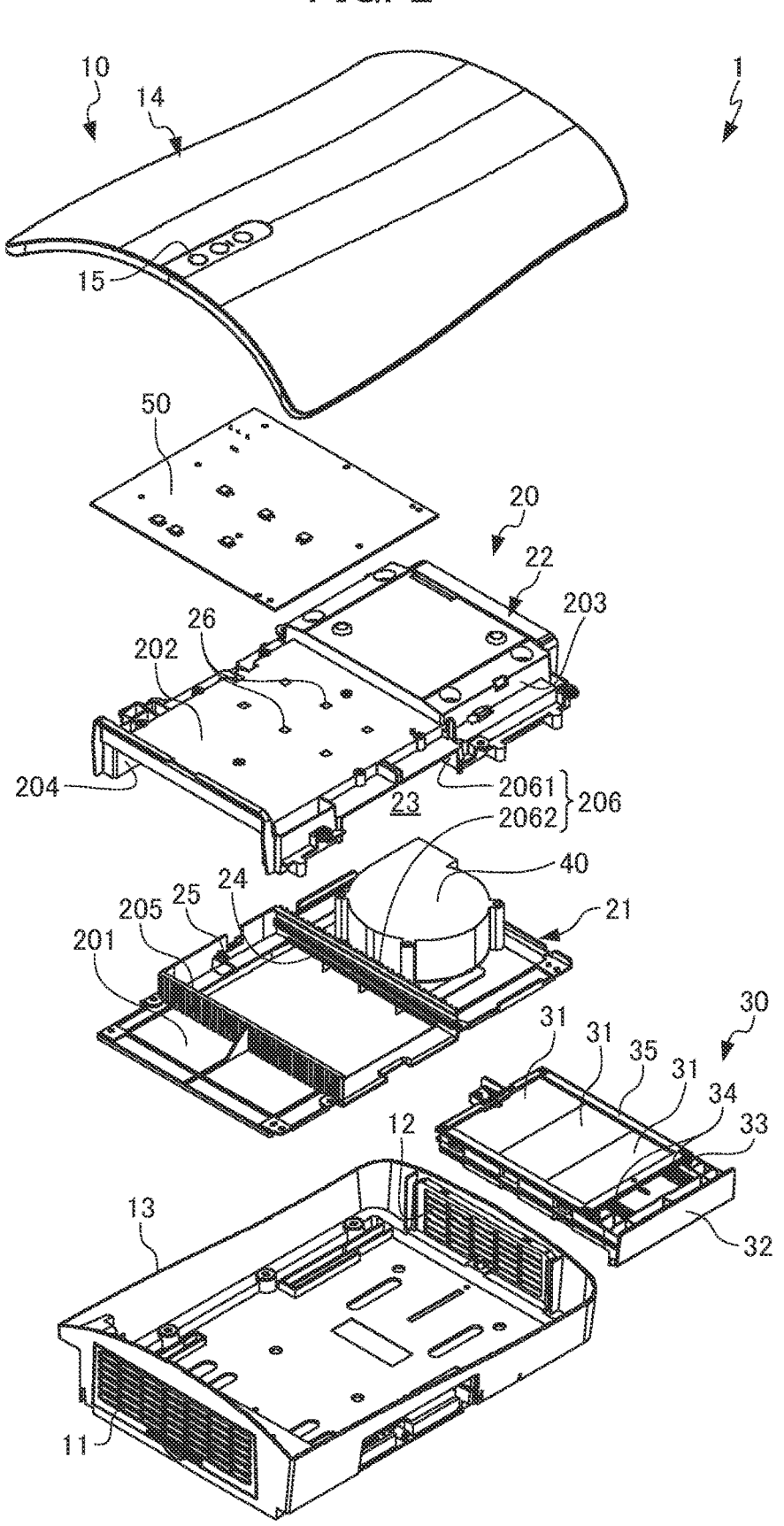
FIG. 2 is an exploded perspective view of the deodorization apparatus of FIG. 1.

An embodiment of the present invention will be described below with reference to the drawings. FIG. 1 is a perspective view illustrating a deodorization apparatus 1 according to one embodiment of the present invention. FIG. 2 is an exploded perspective view of the deodorization apparatus 1, and FIG. 3 is a cross-sectional view of the deodorization apparatus 1.

Figure 3:
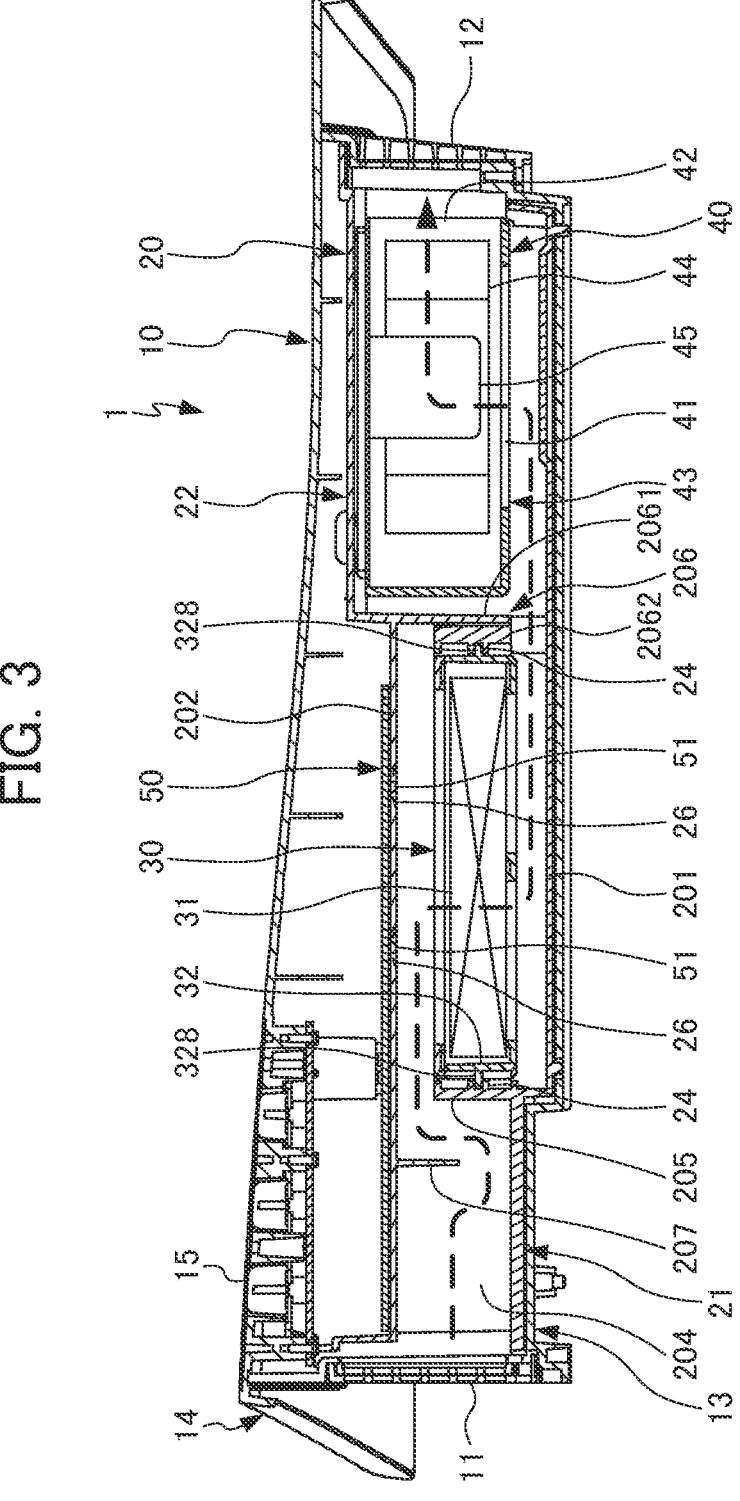
FIG. 3 is a cross-sectional view of the deodorization apparatus of FIG. 1.

The deodorization apparatus 1 of the present embodiment includes: a housing 10 that has an intake port 11 and an outlet port 12; a flow path member 20 that is housed in the housing 10 and defines an airflow path connecting the intake port 11 to the outlet port 12 through a route indicated by the broken arrow in FIG. 3; a plate-shaped photocatalyst unit 30 that is disposed to divide the airflow path into an upstream side and a downstream side and is permeable to air; a centrifugal blower 40 that is accommodated in the airflow path and generates, in the airflow path, an airflow passing through the photocatalyst unit 30; and a circuit board 50 that has a plurality of LEDs 51 mounted thereon and functioning as light sources for emitting light onto the photocatalyst unit 30.

The deodorization apparatus 1 operates in such a manner that the centrifugal blower 40 suctions air into the flow path member 20, the photocatalyst unit 30 decomposes and removes odor components contained in the air, and the air from which the odor components have been removed is discharged to the outside. The deodorization apparatus 1 is adapted to be attached to and used on a wall surface. Specifically, the deodorization apparatus 1 may be disposed with the intake port 11 facing downward, immediately above an odor source, such as a pet toilet disposed beside a wall, and can suction air from near the odor source below the deodorization apparatus 1, deodorize the air, and discharge the deodorized air upward.

The housing 10 may be formed of separable parts including a back cover 13 that mainly covers a backside of the flow path member 20, and a front cover 14 that mainly covers a front side of the flow path member 20. The back cover 13 may be provided with an attachment structure for attachment to a wall, such as an engagement structure that is engageable with a bracket fixed to the wall. In the present embodiment, the front cover 14 is provided with an operation unit 15 having a power button, etc.

The housing 10 may be formed integrally with the flow path member 20. However, for example, in a case where an airflow path having a shape required by resin molding is formed, the exterior design will be subject to some constraints. Therefore, forming the flow path member 20 for defining an airflow path and the housing 10 for covering the flow path member 20 as separate parts contributes to improvement of the design of the deodorization apparatus 1.

The flow path member 20 may be formed of two separable parts including a back half 21 that is disposed adjacent to a back side in an assumed use state, and a front half 22 that is disposed adjacent to a front side in the assumed use state.

The flow path member 20 includes: a first main wall 201 that is to be positioned adjacent to a back surface in the assumed use state; a second main wall 202 that faces the first main wall 201 and is to be positioned adjacent to a front surface; a first side wall 203 and a second side wall 204 each of which seals a space between a side edge of the first main wall 201 and a side edge of the second main wall 202; a first partition wall 205 that is disposed without a gap between the first partition wall 205 and the first main wall 201 and with a gap between the first partition wall 205 and the second main wall 202; a second partition wall 206 that is arranged downstream of the first partition wall 205 and is disposed without a gap between the second partition wall 206 and the second main wall 202 and with a gap between the second partition wall 206 and the first main wall 201; and a light shielding wall 207 that is arranged opposite to the second partition wall 206 with respect to the first partition wall 205 (i.e., disposed toward the intake port 11) and is disposed without a gap between the light shielding wall 207 and the second main wall 202 and with a gap between the light shielding wall 207 and the first main wall 201.

Each of the walls 201 to 207 does not have to be completely planar, and may have a step. For example, in the present embodiment, since the centrifugal blower 40 has a slightly large thickness, the second main wall 202 has a step whereby the distance between the first main wall 201 and the second main wall 202 slightly increases in the portion where the centrifugal blower 40 is disposed. Each of the walls 201 to 207 does not have to be a one-piece wall, and may be formed of a plurality of separable parts. In the present embodiment, the first side wall 203, the second side wall 204, and the second partition wall 206 are each constituted by combining a part formed on the back half 21 and a part formed on the front half 22.

In the flow path member 20, the first main wall 201, the second main wall 202, the first side wall 203, and the second side wall 204 together form a flat quadrangular tubular body having one end opening to the intake port 11 and the other end opening to the outlet port 12. In a portion within the flow path member 20, the first partition wall 205 and the second partition wall 206 locally generate an airflow in a direction in which the first main wall 201 and the second main wall 202 face each other, and hold the photocatalyst unit 30 in the portion. The light shielding wall 207 prevents a user from directly seeing the light of the LEDs 51 disposed adjacent to the second main wall 202, from the outside through the intake port 11 even when the user looks inwardly through the intake port 11.

More specifically, the flow path member 20 holds the photocatalyst unit 30 between the first partition wall 205 and the second partition wall 206 such that the photocatalyst unit 30 is in parallel to, and spaced apart from, the first main wall 201 and the second main wall 202. In order to hold the photocatalyst unit 30 in this manner, the first side wall 203 has, between the first partition wall 205 and the second partition wall 206, an attachment/detachment opening 23 through which the photocatalyst unit 30 is inserted, and the first partition wall 205 and the second partition wall 206 each have a guide 24 for guiding the photocatalyst unit 30. The second side wall 204 is provided with a retaining part 25 for retaining the photocatalyst unit 30. The attachment/detachment opening 23 and the guides 24 that are provided to the flow path member 20 make it easy to attach and detach the photocatalyst unit 30. In the present embodiment, the attachment/detachment opening 23, the pair of guides 24, and the retaining part 25 are all provided on the back half 21 such that a positional relationship is ensured among them. For this reason, in the present embodiment, the second partition wall 206 is composed of a main body 2061 and a structure-adding portion 2062. The main body 2061 is formed on the front half 22 and is integrated with the second main wall 202. The structure-adding portion 2062 is formed on the back half 21 and integrated with the first main wall 201 so as to be able to be disposed on the main body 2061 substantially without forming an airflow path, and is provided with the guide 24. The second main wall 202 has a plurality of light projection apertures 26 which are formed at positions facing the photocatalyst unit 30 and via which the LEDs 51 of the circuit board 50 on the outer side of the second main wall 202 are exposed to the airflow path formed inside the second main wall 202.

The photocatalyst unit 30 has a plate shape overall, is held between the first partition wall 205 and the second partition wall 206 in such a manner as to be substantially parallel to the first main wall 201 and the second main wall 202, and allows air to pass therethrough in the thickness direction, i.e., in a direction from the second main wall 202 to the first main wall 201. Preferably, a distance between the photocatalyst unit 30 and the first main wall 201 and a distance between the photocatalyst unit 30 and the second main wall 202 are each 0.3 times or more and 1.5 times or less the thickness of the photocatalyst unit 30. This configuration allows air to smoothly flow through the photocatalyst unit 30. Moreover, due to this configuration, the first main wall 201 and the second main wall 202 can be disposed at a relatively small distance from each other, and hence, the deodorization apparatus 1 can be made to have a relatively small thickness as a whole.

Figure 4:
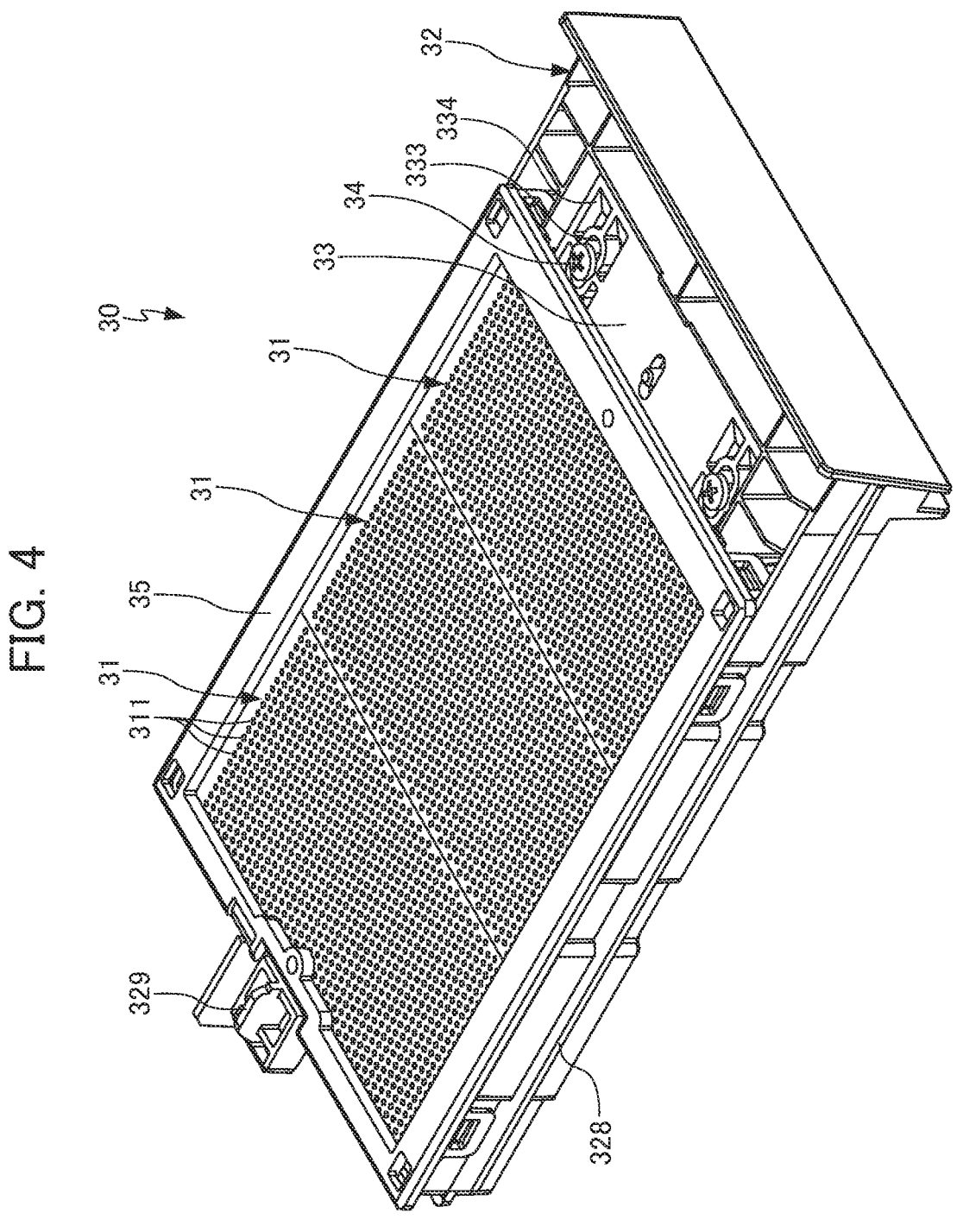
FIG. 4 is a perspective view illustrating a photocatalyst unit of the deodorization apparatus of FIG. 1.
Figure 5:
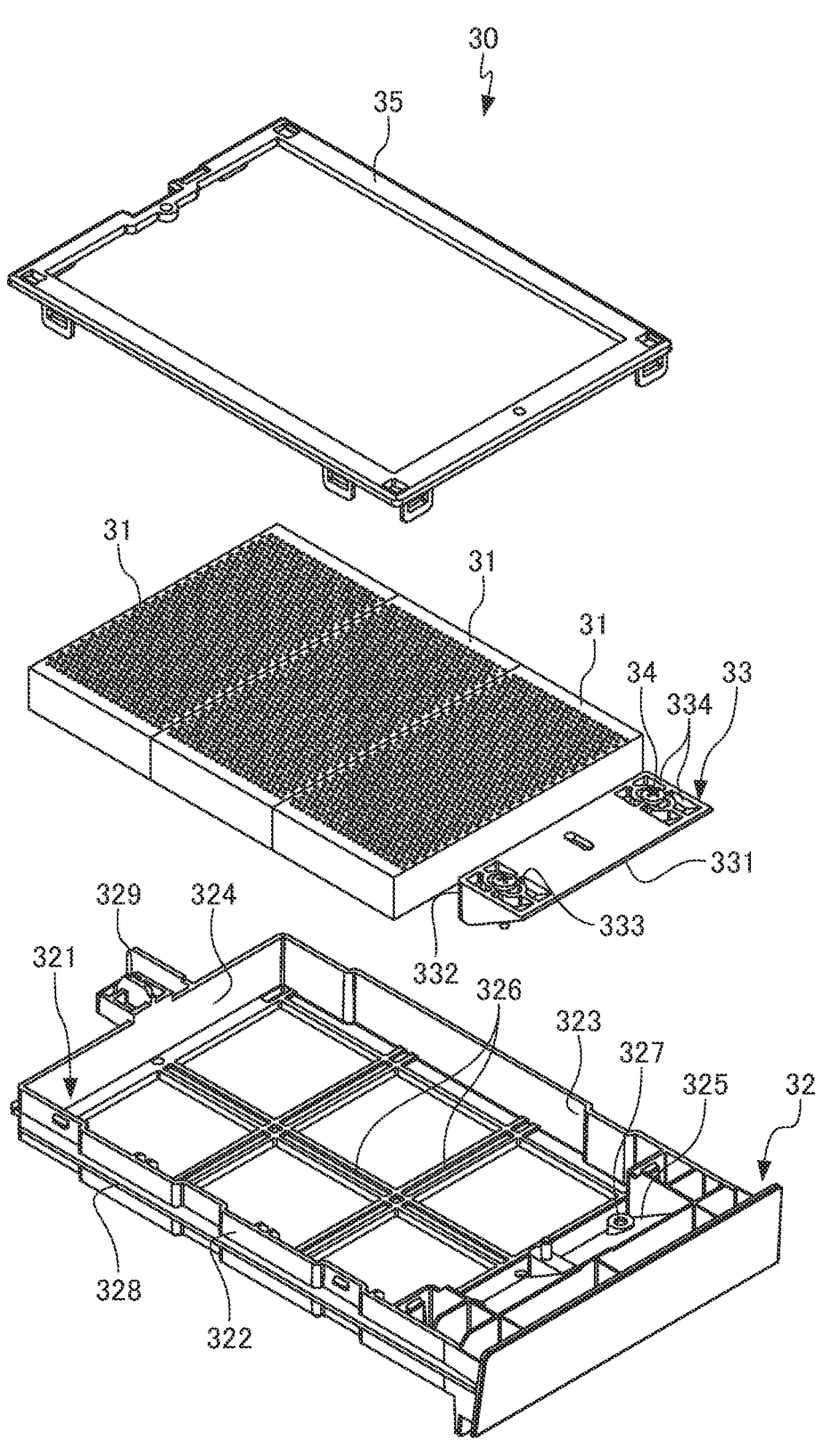
FIG. 5 is an exploded perspective view of the photocatalyst unit of FIG. 4.
Figure 6:
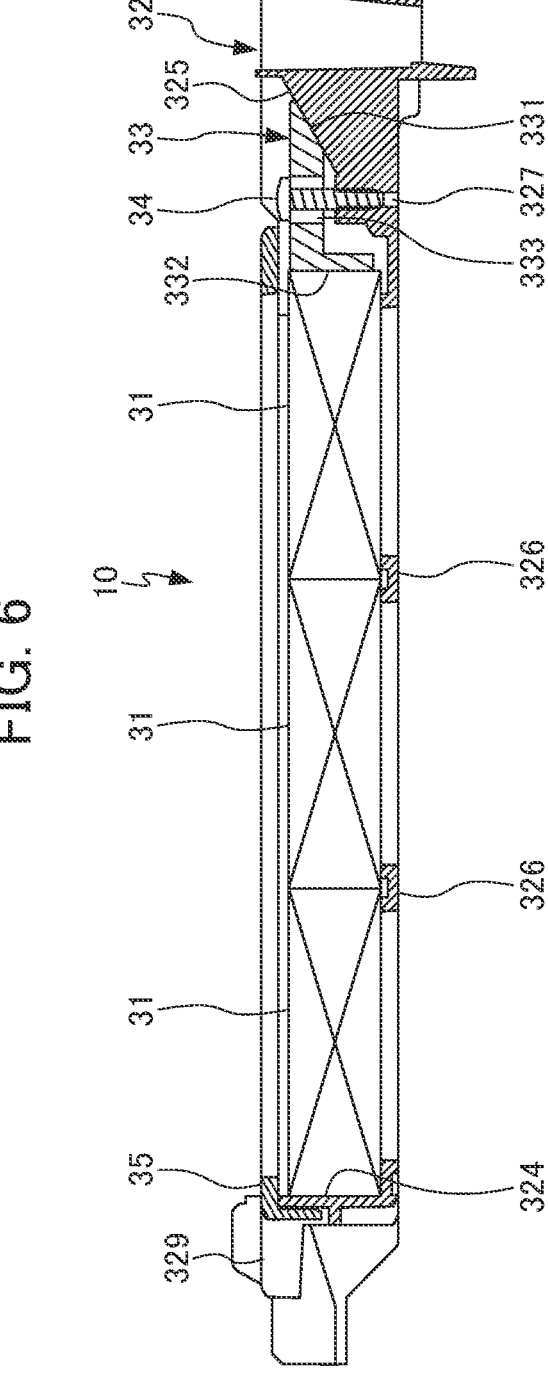
FIG. 6 is a cross-sectional view of the photocatalyst unit of FIG. 4.

As illustrated in the perspective view of FIG. 4, the exploded perspective view of FIG. 5, and the cross-sectional view of FIG. 6, the photocatalyst unit 30 includes: a plurality of photocatalyst carriers 31 each of which includes a rectangular plate-shaped porous ceramic molding and a photocatalyst carried on the porous ceramic molding; a base frame 32 that has an accommodation portion 321 for accommodating the plurality of photocatalyst carriers 31 planarly arranged with their end faces in contact with each other; a pressing member 33 that presses one photocatalyst carrier 31 at one end such that the plurality of photocatalyst carriers 31 accommodated in the accommodation portion 321 are pressed against each other; a fastening member 34 that fastens the pressing member 33 to the base frame 32; and an anti-removal cover 35 that is attached to the base frame 32 and is configured to prevent the photocatalyst carriers 31 from being removed from the accommodation portion 321.

The plurality of photocatalyst carriers 31 mutually inhibit their positional displacement by means of a frictional force generated due to pressure contact therebetween. Furthermore, since the plurality of photocatalyst carriers 31 are held in pressure contact with each other, even if an external force acts on the photocatalyst unit 30 to cause distortion in the overall photocatalyst unit 30, a slight displacement takes place between the photocatalyst carriers 31, whereby stress acting inside each photocatalyst carrier 31 can be reduced. In other words, in a case of using a large photocatalyst carrier, when the base frame 32 is deformed due to a large external force, a relatively large stress acts so that the photocatalyst carrier may also be deformed. In contrast, by collectively holding the plurality of the small photocatalyst carriers 31 while pressing them from opposite sides, deformation of the base frame 32 can be absorbed by displacement between the photocatalyst carriers 31. Thus, even when an impact force is applied to the photocatalyst unit 30 due to falling or the like, damage to the photocatalyst carriers 31 can be effectively suppressed.

Each photocatalyst carrier 31 has a large number of through holes 311 penetrating in the thickness direction, and is permeable to air. The diameter of each through hole 311 may be, for example, 0.5 mm or more and 3.0 mm or less in order to promote contact with air. The pitch of the through holes 311 may be, for example, 1.5 times or more and 3 times or less the diameter of the through hole 311 in order to increase the area of the airflow path while ensuring the strength of the photocatalyst carrier 31.

The thickness of each photocatalyst carrier 31 may be, for example, 10 mm or more and 25 mm or less in order to promote contact with air. The length of the long side of each photocatalyst carrier 31 may be, for example, 50 mm or more and 200 mm or less, and the length of the short side of each photocatalyst carrier 31 may be, for example, 30 mm or more and 100 mm or less. The photocatalyst carriers 31 are preferably arranged such that the long sides thereof are pressed against each other so that movement of the photocatalyst carriers 31 is easily inhibited by a frictional force. Furthermore, it is preferable that the photocatalyst carriers 31 are arranged in one line in the longitudinal direction of the accommodation portion 321, and are pressed against each other in this arrangement direction.

The base frame 32 includes: three vertical restriction surfaces 322, 323, and 324 that define three outer edges of the accommodation portion 321 having a rectangular shape in planar view and adapted to accommodate the photocatalyst carriers 31; an inclined surface 325 disposed to define the remaining outer edge of the accommodation portion 321 and having a normal line inclined toward the accommodation portion 321; and a plurality of crosspieces 326 that partially support the back surfaces of the photocatalyst carriers 31. The inclined surface 325 may have an inclination angle (angle between the normal line of the inclined surface 325 and a normal line of the photocatalyst carrier 31) of, for example, 20° or more and 45° or less. The base frame 32 further includes: a screw hole 327 into which the fastening member 34 is screwed; fitting parts 328 that are slidably fitted to the guides 24 of the flow path member 20; and an engagement part 329 with which the photocatalyst unit 30 is retained to the retaining part 25. The accommodation portion 321 has dimensions larger than the total dimensions of the plurality of photocatalyst carriers 31 to be accommodated so that the accommodation portion 321 can absorb a dimensional error of the photocatalyst carriers 31 and allow a slight positional displacement between the photocatalyst carriers 31. The photocatalyst carriers 31, which are inferior in strength and dimensional accuracy, are held by the base frame 32 that can be made of, for example, a resin molding, thereby making it easy to attach and detach the photocatalyst unit 30 and ensures that air can pass through the photocatalyst carriers 31.

The pressing member 33 has a sliding surface 331 that is in contact with the inclined surface 325, and a pressing surface 332 that presses an end face of the photocatalyst carrier 31. The pressing member 33 of the present embodiment further has a long hole 333 through which the fastening member 34 is inserted, and a plurality of weakening holes 334 formed around the long hole 333.

The pressing member 33 is brought into pressure contact with the base frame 32 in the normal direction of the photocatalyst carrier 31, so that the sliding surface 331 slides on the inclined surface 325, and moves and causes the pressing surface 332 to project toward the photocatalyst carrier 31. In other words, the pressing member 33 is movable toward the accommodation portion 321 while the inclination of the inclined surface 325 forms a pressure angle. As a result, the pressing member 33 and the restriction surface 323 of the base frame 32 that face each other sandwich the photocatalyst carriers 31 arranged in one row, thereby bringing the plurality of photocatalyst carriers 31 into pressure contact with each other.

In the pressing member 33, the peripheral edge of the long hole 333 is pressed by the fastening member 34, and the plurality of weakening holes 334 are formed outside the peripheral edge, whereby a portion around the long hole 333 is easily elastically deformed. Thus, even though the fastening member 34 has a configuration unable to generate a sufficient elastic force as in the present embodiment, the sliding surface 331 is stably in pressure contact with the inclined surface 325, thereby making it possible to generate a pressing force with which the pressing surface 332 presses the photocatalyst carriers 31.

In the present embodiment, the fastening member 34 is a screw that penetrates the long hole 333 to be screwed into a screw hole 327 of the base frame 32, and thereby presses the peripheral edge portion of the long hole 333 toward the base frame 32.

The anti-removal cover 35 engages with the base frame 32, and covers outer edge portions of the photocatalyst carriers 31 accommodated in the accommodation portion 321. The anti-removal cover 35 may also be provided with a crossbar that traverses the accommodation portion 321.

The centrifugal blower 40 includes a casing 43 having a suction port 41 and a discharge port 42, an impeller 44 accommodated in the casing 43, and a motor 45 provided in the casing 43 and rotationally driving the impeller 44. In the centrifugal blower 40, the suction port 41 opens in a rotational axis direction of the impeller 44, and the discharge port 42 opens in a tangential direction of the impeller 44. The centrifugal blower 40 with the above-described configuration has a flat overall shape that is small in axial dimension. Since the centrifugal blower 40 has a relatively high static pressure, it can reliably generate an airflow that passes through the photocatalyst carriers 31 even though the photocatalyst carriers 31 have a relatively large air resistance.

The centrifugal blower 40 is spaced apart from the first main wall 201 such that the suction port 41 opens toward the first main wall 201, and the discharge port 42 opens toward the side opposite to the photocatalyst unit 30 with respect to the second partition wall 206, i.e., toward the outlet port 12. The centrifugal blower 40 may be attached to the first main wall 201 via a spacer, or may be attached to the second main wall 202.

The circuit board 50 having the LEDs 51 mounted on a back surface thereof is disposed in close contact with the outer side of the second main wall 202 so that the LEDs 51 are disposed in the light projection apertures 26 and the light projection apertures 26 are closed. Thus, the LEDs 51 disposed in the light projection apertures 26 of the second main wall 202 do not impede the airflow. Sealing the light projection apertures 26 with the circuit board 50 prevents an unnecessary airflow from being generated.

In the deodorization apparatus 1 having the above-described configuration, air sucked from the outside through the intake port 11 passes through the gap between the first main wall 201 and the light shielding wall 207, and then, the gap between the second main wall 202 and the first partition wall 205, and reaches a front surface of the photocatalyst unit 30. Subsequently, the air penetrates the photocatalyst unit 30, passes through the gap between the first main wall 201 and the second partition wall 206, is sucked into the centrifugal blower 40 through the suction port 41, is blown out through the discharge port 42, and is discharged to the outside through the outlet port 12. That is, in the deodorization apparatus 1, air generally passes along the first main wall 201 and the second main wall 202, but the air turns immediately before the photocatalyst unit 30, immediately after the photocatalyst unit 30, immediately before the centrifugal blower 40, and inside the centrifugal blower 40. Due to this configuration, the deodorization apparatus 1 includes the plate-shaped photocatalyst unit 30 and the flat centrifugal blower 40 that are planarly arranged between the first main wall 201 and the second main wall 202, and consequently, the first main wall 201 and the second main wall 202 can be disposed at a short distance from each other.

While the deodorization apparatus according to one embodiment of the present invention has been described above, the configuration and effects of the deodorization apparatus according to the present invention are not limited to those described above. For example, the deodorization apparatus according to the present invention may include a first main wall adjacent to the front surface and a second main wall adjacent to the back surface. In the deodorization apparatus according to the present invention, light sources may be disposed so as to project inward relative to the second main wall, or may be disposed adjacent to the first main wall.

EXPLANATION OF REFERENCE NUMERALS

1: Deodorization apparatus
10 Housing
11: Intake port
12: Outlet port
13: Back cover
14: Front cover
15 Operation unit
20 Flow path member

8

201: First main wall
202: Second main wall
203: First side wall
204: Second side wall
205: First partition wall
206: Second partition wall
207: Light shielding wall
21: Back half
22: Front half
23: Attachment/detachment opening
24: Guide
25 Retaining part
26: Light projection aperture
30 Photocatalyst unit
31: Photocatalyst carrier
311: Through hole
32: Base frame
321: Accommodation portion
322, 323, 324: Restriction surface
325: Inclined surface
326: Crosspiece
327: Screw hole
328: Fitting part
329: Engagement part
33: Pressing member
331: Sliding surface
332: Pressing surface
333: Long hole
334: Weakening hole
34: Fastening member
35 Anti-removal cover
40 Blower
41: Suction port
42: Discharge port
43: Casing
44: Impeller
45 Motor
50 Circuit board
51: LED (light source)

What is claimed is:

1. A deodorization apparatus comprising:

a first main wall;

a second main wall facing the first main wall;

a first side wall and a second side wall each sealing a space between a side edge of the first main wall and a side edge of the second main wall;

a first partition wall disposed without a gap between the first partition wall and the first main wall and with a gap between the first partition wall and the second main wall;

a second partition wall disposed without a gap between the second partition wall and the second main wall and with a gap between the second partition wall and the first main wall;

a photocatalyst unit provided between the first main wall and the second main wall, and allowing air to pass therethrough in a direction from the second main wall to the first main wall; and a centrifugal blower disposed opposite to the photocatalyst unit with respect to the second partition wall and spaced apart from the first main wall, the centrifugal blower having a suction port that opens toward the first main wall and a discharge port that opens on a side facing away from the second partition wall.

2. The deodorization apparatus according to claim 1, further comprising:

a light source disposed adjacent to the second main wall and configured to emit light onto the photocatalyst unit; and a light shielding wall disposed opposite to the second partition wall with respect to the first partition wall, without a gap between the light shielding wall and the second main wall and with a gap between the light shielding wall and the first main wall.

3. The deodorization apparatus according to claim 2, further comprising:

a circuit board disposed on an outer side of the second main wall and having the light source mounted thereon, wherein the second main wall has a light projection aperture through which the light source is exposed.

4. The deodorization apparatus according to claim 1, wherein the first side wall has, between the first partition wall and the second partition wall, an attachment/detachment opening through which the photocatalyst unit is inserted, and the first partition wall and the second partition wall each have a guide for guiding the photocatalyst unit.

5. The deodorization apparatus according to claim 1, wherein the photocatalyst unit comprises a photocatalyst carrier and a frame that holds the photocatalyst carrier, the photocatalyst carrier including a plate-shaped porous ceramic molding and a photocatalyst carried on the plate-shaped porous ceramic molding.

\*    \*    \*    \*    \*